US00PP20177P3

(12) United States Plant Patent
Vivies

(10) Patent No.: US PP20,177 P3
(45) Date of Patent: Jul. 7, 2009

(54) ***ELAEAGNUS* PLANT NAMED 'VIVELEG'**

(50) Latin Name: *Elaeagnus×ebbingei*
Varietal Denomination: Viveleg

(75) Inventor: Christian Vivies, Toulouse (FR)

(73) Assignee: Selection New Plant Sarl, Le Luc (FR)

( * ) Notice: Subject to any disclaimer, the term of this patent is extended or adjusted under 35 U.S.C. 154(b) by 0 days.

(21) Appl. No.: 11/984,516

(22) Filed: Nov. 19, 2007

(65) Prior Publication Data

US 2009/0133174 P1 May 21, 2009

(51) Int. Cl.
*A01H 5/00* (2006.01)

(52) U.S. Cl. ..... Plt./226
(58) Field of Classification Search ..... Plt./226, Plt./158
See application file for complete search history.

(56) References Cited

PUBLICATIONS

UPOV–ROM GTITM, Plant Variety Database Feb. 2008, GTI Jouve Retrieval Software, Citation for *Elaeagnus* 'Viveleg', one page.*
Telegraph.co.uk, How to grow: *Elaeagnus×ebbingei* 2005 [retrieved on Oct. 14, 2008]. Retrieved from the Internet: <http://www.telegraph.co.uk/gardening/main.jhtml?xml=/gardening/2005/10/15/ghowto15.xml> 2 pages.*

* cited by examiner

*Primary Examiner*—June Hwu
(74) *Attorney, Agent, or Firm*—Buchanan Ingersoll & Rooney PC

(57) ABSTRACT

A new and distinct highly ornamental *Elaeagnus* plant is provided. Unlike common *Elaeagnus ebbingei* plants, the new cultivar displays attractive variegated green leaves that are irregularly margined with yellow. An upright and dense growth habit is displayed. The plant asexually reproduces well through the use of cuttings, and is well suited for providing distinctive ornamentation in the landscape.

2 Drawing Sheets

Botanical/commercial classification: *Elaeagnus×ebbingei/Elaeagnus* Plant.
Varietal denomination: cv. Viveleg.

SUMMARY OF THE INVENTION

*Elaeagnus×ebbingei* is recognized to be an attractive shrub which is believed to have originated in Holland. Such plant is capable of providing ornamentation in the landscape.

The new *Elaeagnus* plant of the present invention was discovered in a plant nursery at Toulouse, France, while growing among common *Elaeagnus×ebbingei* plants (non-patented in the United States). The new cultivar of the present is believed to be a whole plant mutation of unknown causation. I was primarily attracted to a single plant of the present invention in view of its attractive variegated leaves. Had I not discovered and preserved this plant, it would have been lost to mankind.

The new cultivar has been carefully preserved and has been evaluated in order to confirm its distinctive characteristics.

It was found that the new *Elaeagnus* plant displays the following combination of characteristics:

(a) displays an upright and dense growth habit, (b) forms attractive variegated green leaves that are irregularly margined with yellow, and (c) is well suited for providing attractive ornamentation in the landscape.

The new cultivar can be grown to advantage in parks, gardens, and residential settings where a distinctive ornamental shrub is desired.

The new cultivar can be readily distinguished from common *Elaeagnus ebbingei* plants in view of the unusual appearance of the foliage. For example, the common plants of the species display leaves that are of a solid green coloration unlike the variegated green margined with yellow leaves of the new cultivar of the present invention. The new cultivar further can be readily distinguished from the 'Gilt Edge' cultivar (non-patented in the United States) which also displays leaves having a variegated coloration. More specifically, the new cultivar is considerably more vigorous, displays a more upright growth habit, and forms leaves wherein the upper surfaces are darker green in coloration and are irregularly margined with darker yellow.

Asexual reproduction of the new cultivar by the use of cuttings has been carried out at Toulouse, France. Such propagation has confirmed that the unique combination of characteristics of the new cultivar has been stably established and is well transmitted to successive generations. The new cultivar asexually reproduces in a true-to-type manner.

The new cultivar has been named 'Viveleg'.

BRIEF DESCRIPTION OF THE PHOTOGRAPHS

The accompanying photographs show as nearly true as it is reasonably possible to make the same in a color illustration of this character, typical mature plants of the new cultivar at an age of approximately five years while being grown outdoors in the landscape at Toulouse, France.

DETAILED DESCRIPTION

Figure 1:
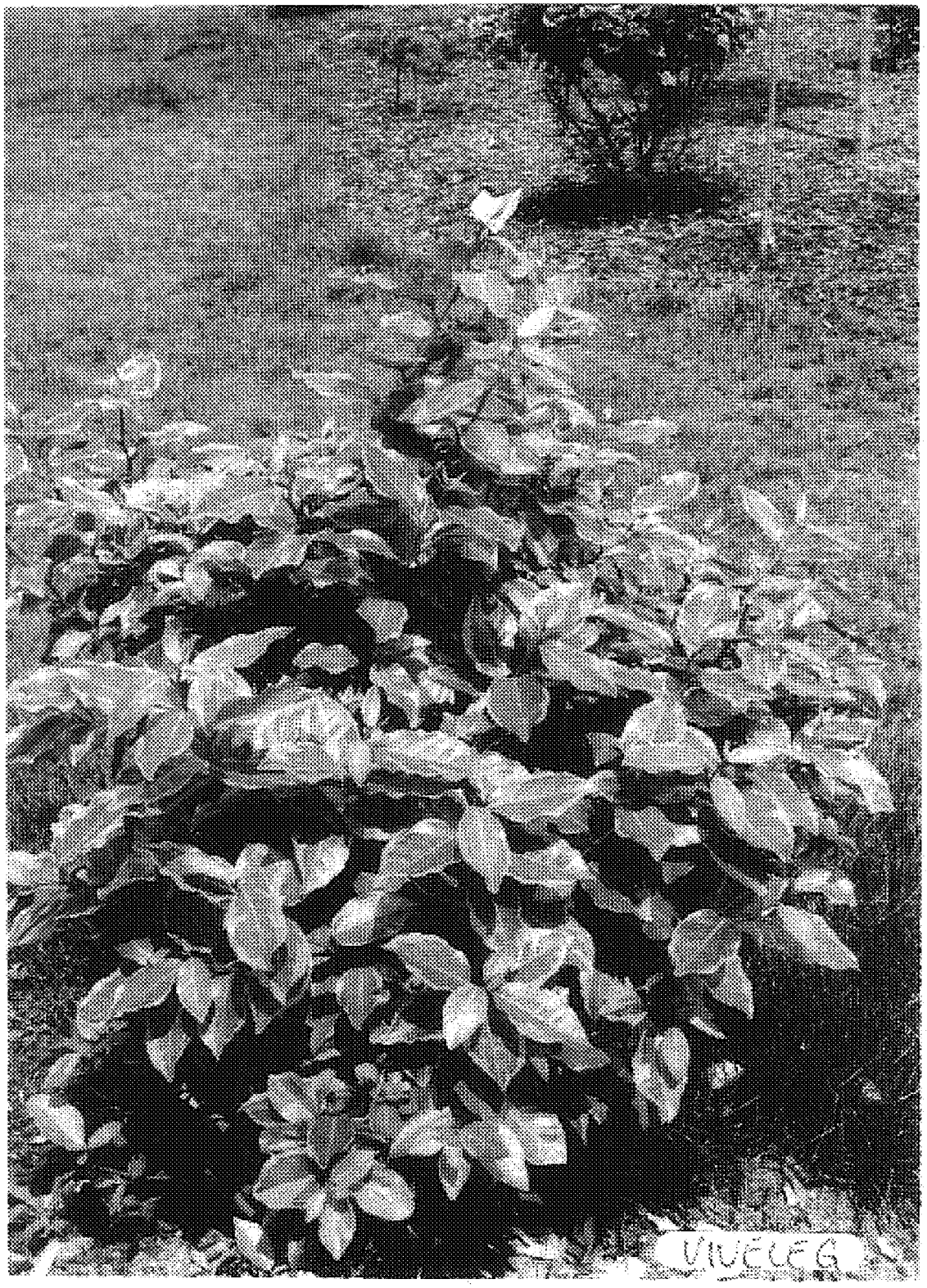
FIG. 1 shows a whole plant of the new cultivar while displaying the upright and dense growth habit.
Figure 2:
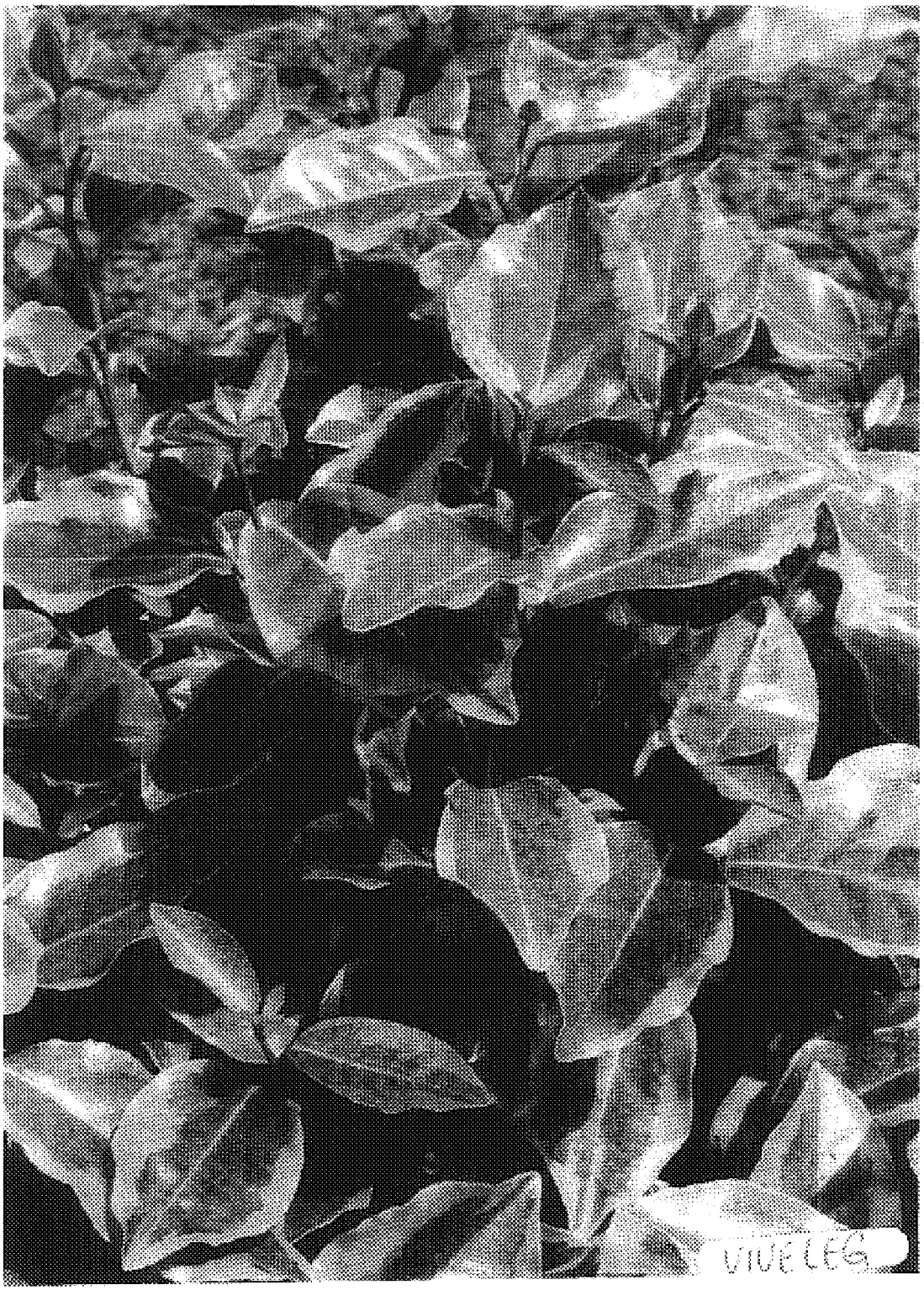
FIG. 2 shows a close view of the distinctive variegated green foliage of new cultivar wherein the green leaves are irregularly margined with yellow.

The following is a detailed description of the new cultivar of the present invention which was prepared while observing mature plants at an age of approximately five years growing outdoors in the landscape during the summer at Toulouse, France. Color terminology is in accordance with the R.H.S. Colour Chart of The Royal Horticultural Society, London, England, except when general color terms are used which are to be accorded their customary dictionary significance.

Type: Shrub for landscape usage.

Plant:

*Type.*—Evergreen.

*Growth habit.*—Upright and dense.

*Height.*—Approximately 2 to 2.5 m on average when mature.

*Width.*—Approximately 1.5 to 2 m on average when mature.

*Branches.*—Near Brown Group 200D in coloration, and somewhat rough in texture.

Foliage:

*Shape.*—Generally elliptic.

*Apex.*—Acute.

*Base.*—Cuneate.

*Margin.*—Somewhat wavy.

*Venation.*—Possesses a prominent central lighter green vein that is near Yellow-Green Group 144-D in coloration.

*Texture.*—Somewhat glossy upper surface, and somewhat rough with tiny scales on both surfaces.

*Color.*—When immature the leaves commonly are near Yellow-White Group 158D on the upper surface and near White Group 155A and White Group 155B on the under surface, and when mature the leaves commonly are near Green Group 137A on the upper surface with irregular margins of Yellow Group 13A and on the under surface near Greyed-White Group 156B in the substantial absence of variegation.

*Petiole.*—Typically approximately 1 to 1.4 cm in length, approximately 2 mm in diameter, rough in texture, and near Grey-Brown Group N199 in coloration.

Inflorescence:

*Blooming.*—Commonly occurs during September and October.

*Configuration.*—As a small bell.

*Size.*—Commonly approximately 8 to 10 mm in length.

*Fragrance.*—Strong and similar to that of Hyacinth and green lemon.

*Lastingness.*—Commonly approximately one month.

*Color.*—Near White Group 155C.

*Drupe.*—Commonly near Red Group 39A, and approximately 1 cm in diameter on average.

Development:

*Disease tolerance/resistance.*—No disease problem has been observed during observations to date.

*Resistance to cold.*—Has withstood temperatures as low as −15° C.

*Resistance to heat.*—Has withstood temperatures as high as 45° C.

The new cultivar has not been observed under all possible environmental condition to date. Accordingly, it is possible that the phenotype may vary somewhat with variation in the environment, such as temperature, light intensity, day length, and other cultural conditions without variance of the genotype.

I claim:

1. A new and distinct *Elaeagnus* plant having the following combination of characteristics:

(a) displays an upright and dense growth habit, (b) forms attractive variegated green leaves that are irregularly margined with yellow, and (c) is well suited for providing attractive ornamentation in the landscape;

substantially as illustrated and described.

* * * * *